Figure 1:
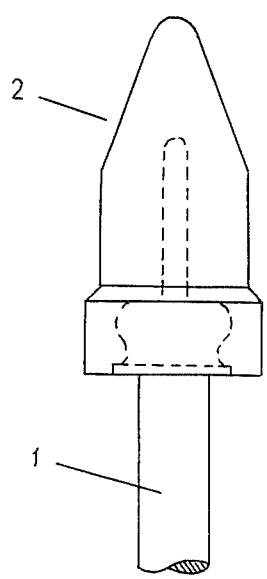

United States Patent [19]

Jarby

[11] 4,185,388
[45] Jan. 29, 1980

[54] HONING AND POLISHING INSTRUMENT ESPECIALLY INTENDED FOR DENTAL USE

[76] Inventor: Sven Jarby, Niels Hemmingsensgade 8, Copenhagen, Denmark

[21] Appl. No.: 835,309

[22] Filed: Sep. 21, 1977

[30] Foreign Application Priority Data

Jun. 17, 1977 [CH] Switzerland .................. 8249/77

[51] Int. Cl.² .................. A61C 3/06; B24D 17/00
[52] U.S. Cl. .................. 433/125; 51/358; 433/166
[58] Field of Search .................. 32/59, 58, 26, 27; 51/383, 382, 372, 375, 376, 377, 358, 393; 403/355, 356, 357, 358, 359, 333, 334, 360, 361, 345; 64/7, 8, 32 F; 279/156, 102, 1 Q; 24/217; 15/424, 42 B, 3.53; 7/124

[56] References Cited

U.S. PATENT DOCUMENTS

| 64,654 | 5/1867 | Floyd | 403/360 |
|---|---|---|---|
| 1,335,825 | 4/1920 | Ellerbeck | 32/58 |
| 1,651,777 | 12/1927 | Peck | 403/360 |
| 2,826,014 | 3/1958 | Field | 51/358 |
| 2,833,576 | 5/1958 | Cirone | 403/334 |
| 3,369,265 | 2/1968 | Halberstadt et al. | 403/334 |
| 3,485,520 | 12/1969 | Alexander | 403/334 |
| 3,614,845 | 10/1971 | Cook | 51/358 |
| 3,740,853 | 6/1973 | Brahler | 32/59 |
| 3,858,368 | 1/1975 | Cocherell et al. | 32/59 |
| 3,907,448 | 9/1975 | Kolibar et al. | 403/361 |
| 3,921,298 | 11/1975 | Fattaleh | 32/59 |

FOREIGN PATENT DOCUMENTS 2230195 12/1972 Fed. Rep. of Germany .

Primary Examiner—Russell R. Kinsey
Assistant Examiner—Michael J. Foycik, Jr.
Attorney, Agent, or Firm—Robert M. Skolnik; William R. Evans; Robert M. Skolnik

[57] ABSTRACT

Honing and polishing instrument especially intended for dental use and being provided with a rotatable shaft. A replaceable honing or polishing unit made of a flexible elastic material can be attached to the free end of the shaft. An undercut indent in the unit embraces a radial sleeve at the free end of the shaft. The shaft also has an end portion extending axially beyond the sleeve which is inserted in a corresponding bore at the bottom of the indent in the unit.

2 Claims, 2 Drawing Figures

U.S. Patent  Jan. 29, 1980  4,185,388

HONING AND POLISHING INSTRUMENT ESPECIALLY INTENDED FOR DENTAL USE

The invention relates to a honing and polishing instrument especially intended for dental use and being provided with a rotatable shaft. On the free end of the shaft a replaceable honing or polishing unit made of a flexible elastic material can be attached. The unit, by way of an undercut indent, embraces a radial sleeve at the end of the shaft.

Honing and polishing units for the instrument described must be made of a relatively soft material allowing easy mounting on and dismounting from the shaft. The honing and polishing units will bend depending on their shape and be deformed when exposed to great working pressures. This is especially so when they are of relatively long and thin shape. Such deformation will destroy the unit, and cause vibrations which will in case of dental treatment cause unpleasant taps against the teeth of a patient.

The object of the invention is to devise a tool so that the applied working pressures can be exerted without any risk of deformation of the honing or polishing unit.

This is according to the invention achieved in that the end part of the shaft is extended axially beyond the sleeve, which extension is inserted in a corresponding bore at the bottom of an indent in the unit.

The end part of the shaft will act as a supporting core to the honing or polishing unit and prevent it from deformation even when the unit is exposed to vigorous lateral force.

It is according to the invention advantageous that the length of the axial extension of the end part of the shaft be greater than the length of the axial extension of the sleeve. Such construction will facilitate the mounting of a unit, because the end part of the shaft will reach into the corresponding bore before the radial sleeve will meet the opening of the undercut indent of the unit.

It may be desirable by the applied working pressures to transfer a substantial moment of rotation from the shaft to the unit. This may according to the invention be achieved by shaping the end part of the shaft and the corresponding bore in the unit non-circular in section. Thus, the unit will, at all times, be carried along by the rotation of the shaft without any slips irrespective of the direction of rotation of the shaft.

Figure 2:
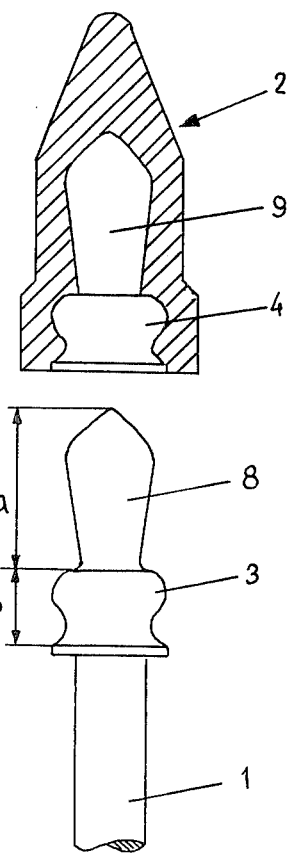

The invention will be described below in detail with reference to the drawing in which FIG. 1 shows a sideview of a honing and polishing instrument according to the inventions, and FIG. 2 shows honing or polishing unit and shaft mutually separated and turned 90 degrees round the longitudinal axis as compared with FIG. 1.

The honing and polishing instrument as shown in FIGS. 1 and 2, comprises a shaft 1 to the free end of which is attached a flexible honing or polishing unit 2, so that the unit by way of an undercut indent 4 is embracing a radial sleeve 3 at the end of the shaft. The sleeve 3 may have plane or rounded off flanks as shown.

The shaft 1 extends axially beyond the sleeve 3 with one end part 8, and the unit 2 is provided with a corresponding bore 9 at the bottom of the indent 4 for mating with part 8. End part 8 and bore 9 are of a non-circular cross-section to ensure that the coupling between the unit 2 and the shaft 1 will remain rotation-safe. The end part 8 will support the mounted unit and prevent it from bending and deformation caused by transversely acting force during the use of the instrument.

For reasons of expediency the dimensions of the sleeve 3 and the end part 8 are slightly exceeding the corresponding dimensions of the indent 4 and the bore 9. By mounting the unit 2 on the shaft 1 the unit 2 can be elastically deformed to fit the shaft tightly. The end part 8 may furthermore be of diminishing cross-section, preferably towards the sleeve 3, so that the unit 2 is secured firmly against axial displacement.

To prevent damaging of the relatively soft unit 2 during the mounting procedure on the end part 8, the latter is as shown rounded off.

The length "a" of the end part 8 can as shown in the drawing exceed the length "b" of the sleeve 3. This will facilitate the insertion of the end part 8 into the bore 9.

I claim:

1. A rotatable honing and polishing instrument comprising;
    a rotatable shaft;
    connection means formed at one end of said shaft for connecting and supporting a flexible honing and polishing unit on said shaft, said connecting means including a flange of circular cross section coupled to said shaft, and a thin flat elongated extension of a generally trapezoidal cross section shape coupled to said flange, and
    a replaceable honing and polishing unit of flexible abrasive material, said unit having a hollow internal portion including a bore shaped to fit over said extension and an indent shaped to fit over said flange, the generally trapezoidal cross section shape of said bore and said flat extension thereby limiting lateral flexing of the honing and polishing unit during use and slippage of said honing and polishing unit during rotation of said shaft, said extension being of a length which is greater than the length of said flange so that during insertion of said flexible unit on said connecting means, said extension is the first to contact said flexible unit thereby to facilitate the connection of said unit to said shaft.

2. Connecting means for coupling a flexible rotatable honing and polishing instrument to a driving shaft comprising;
    a rotatable shaft;
    connection means formed at one end of said shaft for coupling said shaft to and supporting a flexible polishing element said connecting means including a flange of circular cross section coupled to said shaft, and a thin flat elongated extension of generally trapezoidal cross section shape coupled to said flange, the shape of said extension thereby limiting lateral flexing of the flexible unit and slippage of said unit during rotation of said shaft, said extension being of a length which is greater than the length of said flange so that during insertion of said flexible unit on said connecting means, said extension contacts said flexible unit before said flange thereby to facilitate the connection of said unit to said shaft.

* * * * *